United States Patent [19]
Starchevich

[11] Patent Number: 5,718,409
[45] Date of Patent: Feb. 17, 1998

[54] FLOW REGULATOR

[76] Inventor: Jovanka Starchevich, 138 Sullivan St., New York, N.Y. 10012

[21] Appl. No.: 759,438

[22] Filed: Dec. 5, 1996

[51] Int. Cl.⁶ .................................................. F16K 7/06
[52] U.S. Cl. .................................................. 251/6; 251/4
[58] Field of Search ................................... 251/4, 6

[56] References Cited

U.S. PATENT DOCUMENTS

| | | |
|---|---|---|
| 3,297,558 | 1/1967 | Hillquist .............................. 251/6 X |
| 3,625,472 | 12/1971 | Rychlik .............................. 251/6 |
| 3,685,787 | 8/1972 | Adelberg . |
| 4,013,263 | 3/1977 | Adelberg . |
| 4,047,694 | 9/1977 | Adelberg . |
| 4,475,709 | 10/1984 | Becker, Jr. . |
| 4,725,037 | 2/1988 | Adelberg . |
| 4,974,811 | 12/1990 | Ishida . |
| 5,014,962 | 5/1991 | Adelberg . |

*Primary Examiner*—John Fox
*Attorney, Agent, or Firm*—McAulay Fisher Nissen Goldberg & Kiel, LLP

[57] ABSTRACT

A flow regulator has a pair of side walls extending generally parallel to one another, a bottom wall connecting the side walls to one another and defining an elongate channel for receiving a compressible tube, a roller rotatably and shiftably mounted to the side walls for rolling along the tube in the channel and compressing the tube against the bottom wall. The bottom wall is provided with a formation which varies from a first end of the channel towards an opposite, second end thereof, whereby compressive force applied to the tube via the roller is different at different longitudinal positions of the roller along the channel. A bracket is disposed about the side walls at one end of the channel. The bracket is in contact with outer surfaces of the side walls only in regions of the side walls spaced from the bottom wall.

13 Claims, 1 Drawing Sheet

5,718,409

1

FLOW REGULATOR

BACKGROUND OF THE INVENTION

This invention relates to a flow regulator. More particularly, this invention relates to a flow regulator of the type which compresses a tube to vary a flow rate of a fluid passing through the tube. Even more particularly, this invention relates to a flow regulator of the roller type. The invention is useful in medical applications, to control the flow rate of intravenous fluids, parenteral fluids, blood, plasma, etc.

Intravenous tubes have been widely used for supplying nutrients and medication to patients. Most existing, manually adjustable clamps for regulating the flow rate through an intravenous tube have a high degree of inaccuracy, particularly after the clamped tubing has been in use for a period of time in excess of one hour. In addition, existing manually actuated clamps cannot be used where the fluid being delivered through the tubing is viscous, for example, blood. If a substantial degree of accuracy in flow rate maintenance is required, it has been necessary to utilize an expensive pump system. Even pumps systems are limited in their accuracy.

A particularly common kind of flow regulator in medical applications is the so-called Adelberg clamp which uses the combination of an inclined plane or V-grooved surface and a roller that is moved along the inclined plane or grooved surface to variably compress the tube to allow more or less liquid to flow through the tube. Although widely used, the Adelberg clamp is inaccurate and unreliable so as to require continual monitoring and adjustment to maintain a desired flow rate.

OBJECTS OF THE INVENTION

An object of the present invention is to provide an improved manually adjustable flow regulator of the above-described roller type.

Another object of the present invention is to provide a manually adjustable flow regulator which has enhanced accuracy and reliability.

An additional object of the present invention is to provide such a flow regulator which is inexpensive and easy to manufacture.

A further object of the present invention is to provide a manually adjustable flow regulator which is utilizable where a medical fluid is to be delivered through a flexible tube.

These and other objects of the present invention will be apparent from the descriptions and illustrations herein.

BRIEF DESCRIPTION

A flow regulator comprises, in accordance with the present invention, a pair of side walls extending generally parallel to one another, a bottom wall connecting the side walls to one another and defining an elongate channel for receiving a compressible tube, a roller rotatably and shiftably mounted to the side walls for rolling along the tube in the channel and compressing the tube against the bottom wall. The bottom wall is provided with a formation which varies from a first end of the channel towards an opposite, second end thereof, whereby compressive force applied to the tube via the roller is different at different longitudinal positions of the roller along the channel. A bracket is disposed about the side walls at one end of the channel. The bracket is in contact with outer surfaces of the side walls only in regions of the side walls spaced from the bottom wall.

2

The bracket is preferably disposed at the end of the flow regulator where the tube is subjected to the greatest compressive forces and the controlled flow rate is the lowest. The bracket prevents an undue flexing of the side walls away from each other under forces exerted by the roller and the compressed tube.

In accordance with a feature of the present invention, it is contemplated that the side walls at the bracketed end of the channel are connected to one another only by the bottom wall at one side and the bracket at an opposite side. Thus, the web or strut which extends between the side walls at the low-flow-rate end of a conventional regulator is omitted.

Pursuant to another feature of the invention, the bracket includes portions spaced from the side walls in a region about the bottom wall.

In a specific embodiment of the present invention, the bracket is substantially U-shaped with legs having free ends provided with fingers contacting the bottom wall. The fingers are substantially colinear and oriented towards one another.

In accordance with a further feature of the present invention, the side walls are provided along inwardly facing surfaces with respective grooves, the roller having a pair of shaft elements extending laterally in opposing directions along an axis of the roller, each of the shaft elements being provided at a free end with a friction enhancing formation. The friction enhancing formation may take the form of knurling, a layer of high friction material, embedded grit particles, or a series of axially extending ridges and interleaved longitudinal grooves.

In accordance with a yet another feature of the present invention, the flow regulator further comprises a pointer member coupled with the roller to move therewith as the roller negotiates the channel. A series of marks are disposed along the outer surface of one of the side walls for cooperating with the pointer to provide an indication of flow rate.

In accordance with an additional feature of the present invention, at least one of the sidewalls is provided with a seat receiving the bracket. The seat may be defined by a recess in the side wall or a shoulder on the side wall. The seat assists in retaining the bracket on the regulator.

The bracket may be bonded to one or both of the side walls, for example, by ultrasonic welding.

A manually adjustable flow regulator in accordance with the present invention provides substantially enhanced accuracy and reliability. The improved performance results from the addition of a single part to existing roller-type clamps. Accordingly, the flow regulator of the present invention is inexpensive and easy to manufacture. A manually adjustable flow regulator in accordance with present invention is utilizable where a medical fluid, for example, a parenteral solution, saline, plasma or blood, is to be delivered through a flexible tube.

DESCRIPTION OF THE PREFERRED EMBODIMENTS

Figure 1:
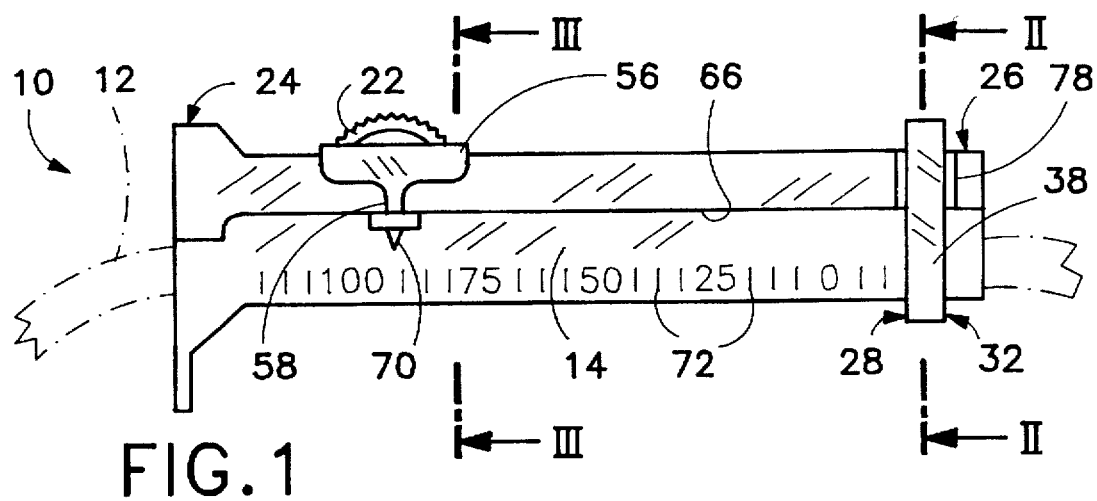
FIG. 1 is a side elevational view, on an enlarged scale, of an intravenous flow regulator in accordance with the present invention.

The drawings illustrate a flow regulator 10 intended for use with a compressible medical feed tube 12. The tube can deliver saline, blood, plasma, total parenteral fluids and other liquids to a patient, for example, to a blood vessel of the patient. Regulator 10 has a pair of side walls 14 and 16 which extend generally parallel to one another. A bottom wall 18 extends substantially the length of side walls 14 and 16 and connects the side walls to one another to define an elongate channel 20 for receiving tube 12. Channel 20 is generally open towards one side, as indicated at 21 in FIG. 3.

A roller 22 is rotatably and shiftably mounted to side walls 14 and 16. Roller 22 is partially disposed in channel 22 and partially extends through opening 21 for enabling the manual application of a torque to roller 22. Roller 22 is in frictional engagement with tube 12 for rolling along the tube in channel 20, under the manual application of torque, and compressing tube 12 against bottom wall 18. Bottom wall 18 is provided with a conventional formation such as a ramp (not shown) and/or a tapered V-shaped groove (not shown) which has a shape varying from a first end 24 of regulator 10 (and channel 20) towards an opposite, second end 26 thereof. Thus, compressive force applied to tube 12 via roller 22 is different at different longitudinal positions of roller 22 along channel 20.

A bracket assembly 28 is disposed about side walls 14 and 16 at the one end 26 of channel 20. End 26 is that terminal portion of flow regulator 10 where tube 12 is subjected to the greatest compressive forces and the controlled flow rate is the lowest. Bracket assembly 28 serves to prevent an undue flexing of side walls 14 and 16 away from one another under the forces exerted by roller 22 and compressed tube 12. This bracing action of bracket assembly 28 limits side wall flexing at virtually all longitudinal positions of roller 22 along channel 20.

Bracket assembly 28 is in contact with outwardly facing surfaces (not labeled) of side walls 14 and 16 only in regions thereof spaced from bottom wall 18. More particularly, bracket assembly 28 includes an inner U-shaped bracket element 30 and an outer U-shaped bracket element 32. Bracket elements 30 and 32 may be a unitary injected molded polymeric piece or two separate polymeric pieces joined by ultrasonic or heat welding before or after assembly to side walls 14 and 16. Inner bracket element 30 engages side walls 14 and 16 only along free edges and outer surfaces thereof spaced from bottom wall 18. Outer bracket member 32 surrounds inner bracket element 30, as well as side walls 14 and 16 and bottom wall 18. Outer bracket element 32 is spaced from side walls 14 and 16 by virtue of inner bracket element 20. In particular, there are gaps 34 and 36 between outer bracket element 32 and side walls 14 and 16 in region about bottom wall 18.

Figure 3:
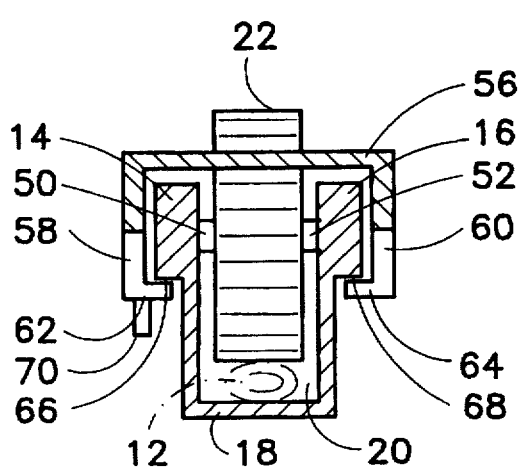
FIG. 3 is a transverse cross-sectional view, on a similarly large scale, taken along line III—III in FIG. 1.

As shown in FIG. 3, side walls 14 and 16 at the bracketed end 26 of regulator 10 and channel 20 are connected to one another only by bottom wall 18 at one side and bracket assembly 28 at an opposite side. There is no web or strut extending between side walls 14 and 16 at the low-flow-rate end 26 as there is in conventional flow regulators.

Outer bracket element 32 has legs 38 and 40 having free ends provided with fingers 42 and 44 which are in contact with bottom wall 18. Fingers 42 and 44 are substantially colinear and oriented towards one another.

Figure 5:
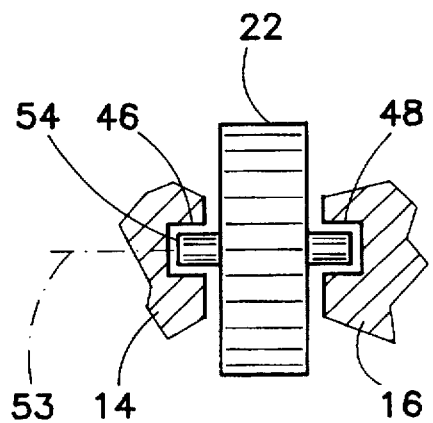
FIG. 5 is a front view of the roller of FIG. 1 and a pair of axle members, showing the axle members projecting into tracks or grooves in side walls of the flow regulator.

Side walls 14 and 16 are provided along inwardly facing surfaces (not labeled) with respective grooves 46 and 48 (FIG. 5) as in conventional intravenous flow regulators. Roller 22 has a pair of axle or shaft elements 50 and 52 extending laterally in opposing directions along an axis 53 of roller 22. Each shaft element 50 and 52 is provided at a free end with friction enhancing longitudinal ridges 54 defined by interleaved longitudinal grooves (not separately labeled). The friction enhancing function of ridges 54 may be performed by other formations such as knurling, a layer of high friction material, or embedded grit particles.

Figure 4:
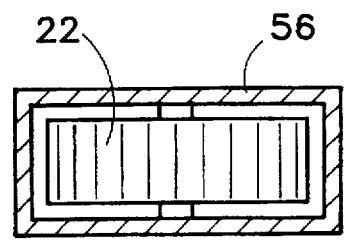
FIG. 4 is a top plan view of a roller member and a slidable frame entrained thereto, both shown in FIG. 1.

As illustrated in FIGS. 1, 3 and 4, flow regulator 10 is provided with a rectangular frame 56 traversed by roller 22. Frame 56 is entrained to roller 22 to travel therewith along channel 20. Frame 56 has one or two arms 58 and 60 which extend generally in parallel along respective side walls 14 and 16 and which are provided at free ends with inwardly turned hooks 62 and 64. Hooks 62 and 64 engage respective longitudinally extending shoulders 66 and 68 on side walls 14 and 16 to thereby anchor frame 56 to the side walls of the flow regulator. A pointer member 70 projecting from one arm 58 is coupled via frame 56 to roller 22 to move therewith as the roller negotiates channel 20. A series of marks 72 are disposed along the outer surface of side wall 14 for cooperating with pointer 70 to provide an indication of flow rate.

Figure 2:
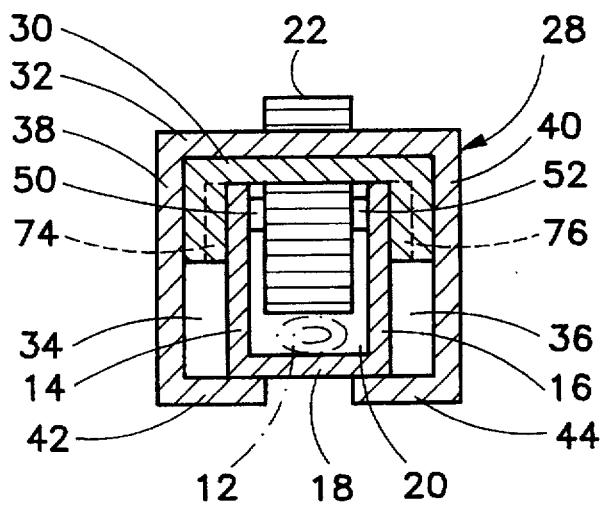
FIG. 2 is a transverse cross-sectional view, on a larger scale, taken along line II—II in FIG. 1.

As shown in FIG. 2, side walls 14 and 16 are formed with respective recesses 74 and 76 which define seats receiving inner bracket element 30. Recesses or seats 74 and 76 assist in retaining the bracket assembly 28 on regulator side walls 14 and 16. More specifically, side walls 14 and 16 have stops or lips 78 (see FIG. 1) at regulator end 26 for preventing the bracket assembly 28 from sliding off the flow regulator. This feature is particularly useful where bracket assembly 28 is retrofitted to a pre-existing flow regulator. In addition, bracket assembly 28 may be bonded to one or both side walls 14 and 16, for example, by ultrasonic welding.

A flow regulator as described herein has been tested using a McGaw 1000 cc D5W plastic IV solution bag, a standard McGaw 87 inch microdrip (60 gtts) IV tubing, and a 19 gauge 1½ inch metal needle. The test was conducted at a temperature of 75° F., a drip chamber height of 36 inches above an infusion site, and a flow regulator height of 5 inches below the bottom of the drip chamber. During a test period of four hours, a count of 30 drops was made every thirty minutes with an extra count at ten minutes after the initial count. The time in seconds for counting thirty drops was recorded at each count. The difference in seconds from the initial count and the percent change were calculated and recorded. The average change in the 30 drop time over the four hour period was 0.81 seconds and the average percent changes was 0.31%.

Although the invention has been described in terms of particular embodiments and applications, one of ordinary skill in the art, in light of this teaching, can generate additional embodiments and modifications without departing from the spirit of or exceeding the scope of the claimed invention. For example, frame or carriage 56 may take different forms, the function of pointer 70 may be performed by arm 58, and recesses or seats 74 and 76 may be replaced by beads or other stop elements on side walls 14 and 16.

Also, it is to be understood that inner bracket 30 may be used alone, without outer bracket 32, to perform the functions of bracket assembly 28. In that event, bracket 30 is preferably bonded to flow regulator side walls 12 and 14, whether by adhesive and/or ultrasonic welding or other technique. Where bracket assembly 28 is retrofitted to a pre-existing flow regulator 10, outer bracket 32 may be held onto inner bracket by friction, adhesive and/or stop 78.

Accordingly, it is to be understood that the drawings and descriptions herein are proffered by way of example to facilitate comprehension of the invention and should not be construed to limit the scope thereof.

What is claimed is:

1. A flow regulator comprising:
   a pair of side walls extending generally parallel to one another;
   a bottom wall connecting said side walls to one another and defining an elongate channel for receiving a compressible tube;
   a roller rotatably and shiftably mounted to said side walls for rolling along the tube in said channel and compressing the tube against said bottom wall, said bottom wall being provided with a formation which varies from a first end of said channel towards an opposite, second end thereof, whereby compressive force applied to said tube via said roller is different at different longitudinal positions of said roller along said channel; and
   a bracket disposed about said side walls at one end of said channel, said bracket being in contact with outer surfaces of said side walls only in regions of said side walls spaced from said bottom wall.

2. The flow regulator defined in claim 1 wherein said bracket includes portions spaced from said side walls in a region about said bottom wall.

3. The flow regulator defined in claim 2 wherein said bracket is substantially U-shaped with legs having free ends provided with fingers contacting said bottom wall.

4. The flow regulator defined in claim 3 wherein said fingers are substantially colinear and oriented towards one another.

5. The flow regulator defined in claim 4 wherein said side walls at said one end of said channel are connected to one another only by said bottom wall at one side and said bracket at an opposite side.

6. The flow regulator defined in claim 1 wherein said bracket is substantially U-shaped.

7. The flow regulator defined in claim 1 wherein said side walls at said one end of said channel are connected to one another only by said bottom wall at one side and said bracket at an opposite side.

8. The flow regulator defined in claim 1 wherein said side walls are provided along inwardly facing surfaces with respective grooves, said roller having a pair of shaft elements extending laterally in opposing directions along an axis of said roller, each of said shaft elements being provided at a free end with a friction enhancing formation.

9. The flow regulator defined in claim 8 wherein said friction enhancing formation is a series of axially extending ridges.

10. The flow regulator defined in claim 1, further comprising a pointer member coupled with said roller to move therewith as said roller negotiates said channel, also comprising a series of marks disposed along the outer surface of one of said side walls for cooperating with said pointer to provide an indication of flow rate.

11. The flow regulator defined in claim 1 wherein at least one of said sidewalls is provided with a seat receiving said bracket.

12. The flow regulator defined in claim 1 wherein said seat includes a groove in said one of said sidewalls.

13. The flow regulator defined in claim 1 wherein the bracket is disposed at an end of the flow regulator where the tube is subjected to the greatest compressive forces and the controlled flow rate is the lowest.

* * * * *